United States Patent [19]

Kanner et al.

[11] Patent Number: 5,551,442
[45] Date of Patent: Sep. 3, 1996

[54] ACTIVATION ARRANGEMENT WITH SAFETY LOCK-OUT FOR TISSUE SAMPLING INSTRUMENT

[75] Inventors: Rowland W. Kanner; Richard M. Davis, both of Guntersville, Ala.

[73] Assignee: Ryder International Corporation, Arab, Ala.

[21] Appl. No.: 243,979

[22] Filed: May 17, 1994

[51] Int. Cl.$^6$ .................................................. A61B 10/00
[52] U.S. Cl. .......................................... 128/754; 128/749
[58] Field of Search ................................. 128/749, 750, 128/751, 752, 753, 754

[56] References Cited

U.S. PATENT DOCUMENTS

| | | | |
|---|---|---|---|
| 3,989,033 | 11/1976 | Halpern et al. | 128/754 |
| 4,600,014 | 7/1986 | Beraha | 128/754 |
| 4,766,907 | 8/1988 | De Groot et al. | 128/754 |
| 4,958,625 | 9/1990 | Bates et al. | 128/754 |
| 5,121,751 | 6/1992 | Panalletta | 128/754 |
| 5,284,156 | 2/1994 | Schramm et al. | 128/754 |

Primary Examiner—Sam Rimell
Attorney, Agent, or Firm—Trexler, Bushnell, Giangiorgi & Blackstone, Ltd.

[57] ABSTRACT

An actuator device for propulsion of a needle assembly particularly employed for tissue sampling procedures includes a movable drive structure for propelling tissue sampling displacement of the needle assembly and a cocking structure arranged to reverse the displacement of the drive structure after the needle propulsion. A trigger structure in the actuator device cooperates with the drive structure to selectively activate the needle propulsion, and the trigger structure comprises a retention mechanism for releasably restraining the propulsion. The trigger structure also includes safety lock structure which releasably locks the activation restraint by the retention mechanism, and the cocking structure has release structure for unlocking the restraint by the retention mechanism to selectively allow operation of the trigger structure to activate propulsion by the drive structure.

13 Claims, 3 Drawing Sheets

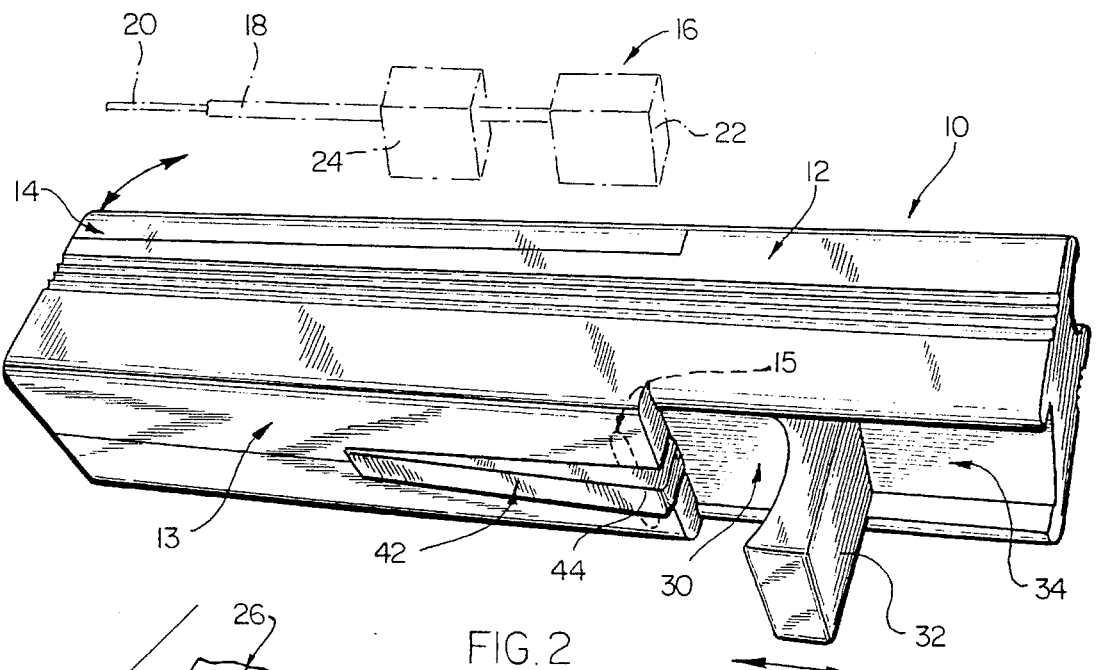
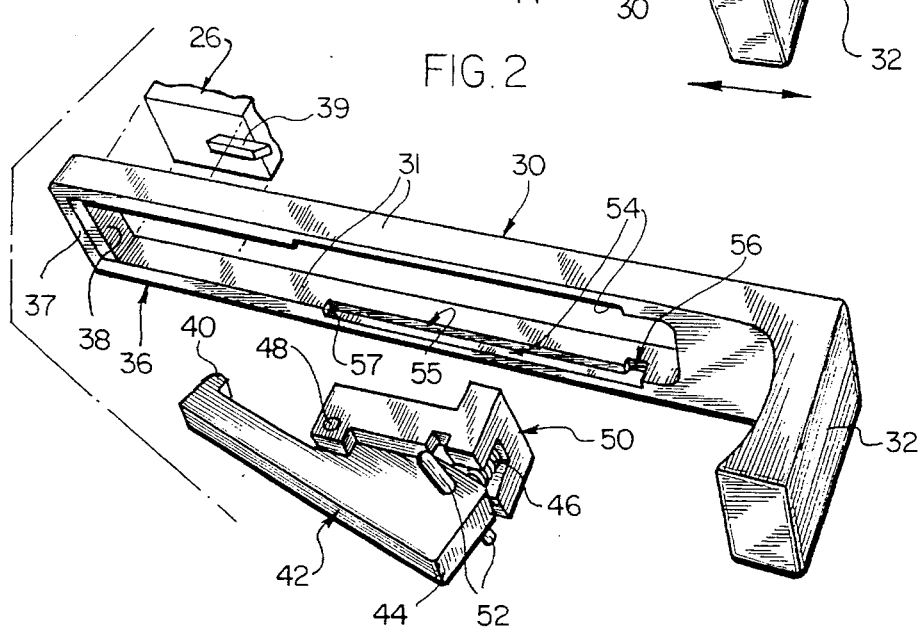
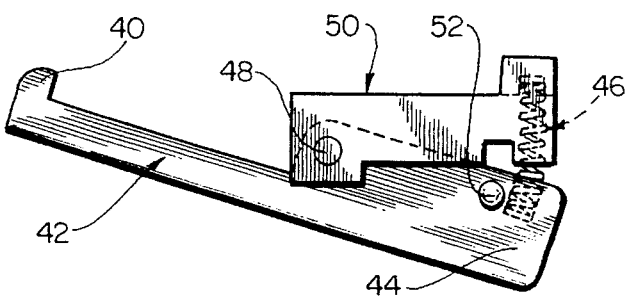
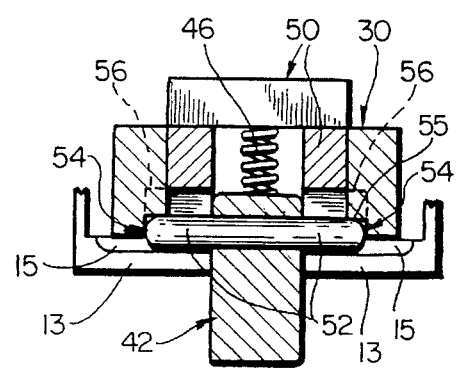

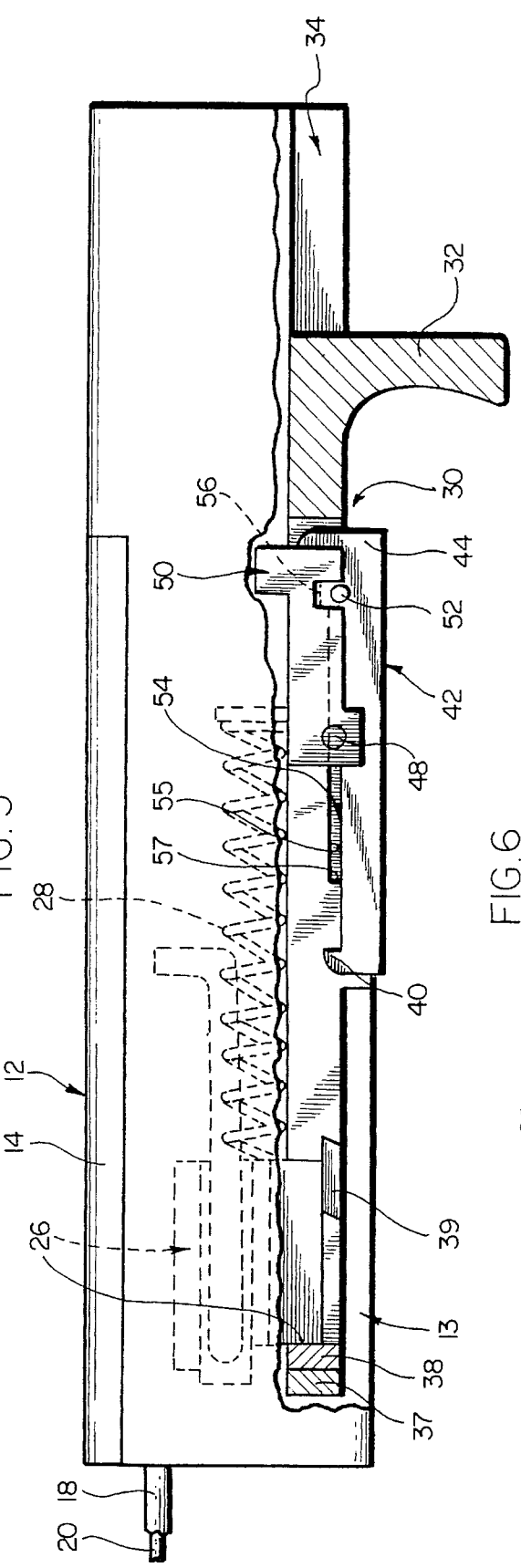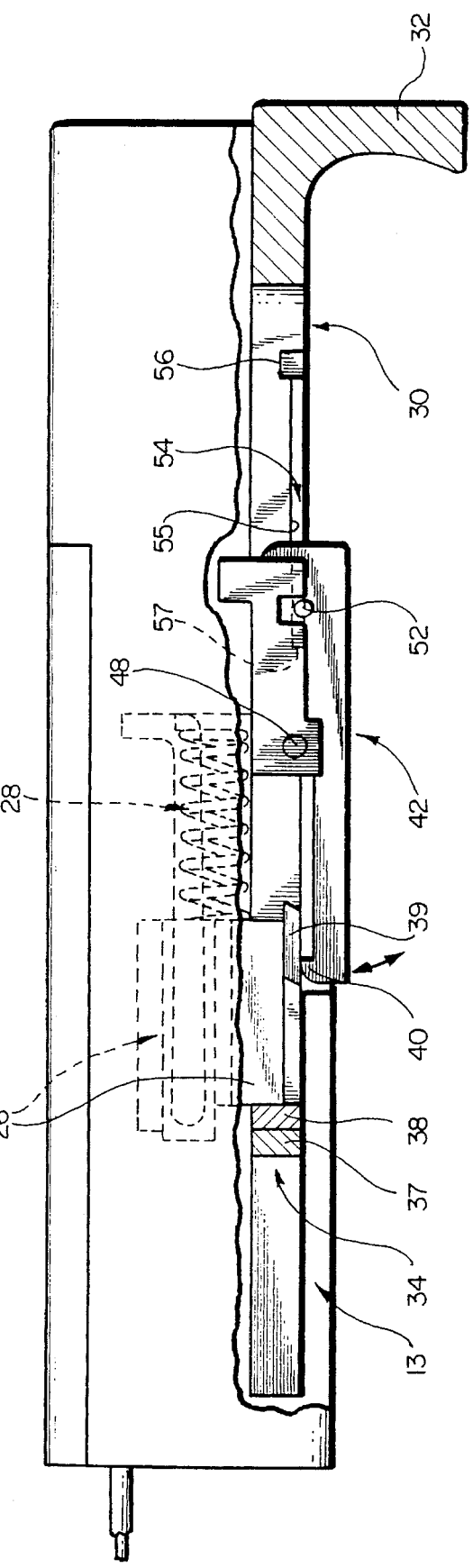

5,551,442

ACTIVATION ARRANGEMENT WITH SAFETY LOCK-OUT FOR TISSUE SAMPLING INSTRUMENT

BACKGROUND OF THE INVENTION

The present invention relates to instruments for obtaining tissue samples to be used for example in biopsy procedures. More particularly, the invention relates to improved instruments for propelling needle assemblies in the diagnostic tissue sampling operation.

In the effort to improve diagnostic tissue sampling, particularly of prostate tissue, needle assemblies have been developed which capture longitudinal, or core sample of the tissue which is extracted for diagnosis. Conventionally, a two-part needle assembly having an outer cannula and inner stylet are employed to cut and capture a core of the tissue as described for example in U.S. Pat. No. 4,776,346. Such instruments have been improved to enable relative propulsion of the two-parts of the needle assembly employing a drive carriage within the instrument which is propelled by a single drive spring expanded and compressed with reversible motions which are conveniently operated manually by the physician as described in U.S. Pat. No. 5,121,751, the disclosure of which is incorporated by a reference for complete description of the needle drive mechanism and operation. These instruments can be provided with improved arming and activation arrangement with safety lock-out structure, in accordance with the present invention.

SUMMARY OF THE INVENTION

In accordance with the present invention, an actuator device for propulsion of a needle assembly particularly employed for tissue sampling procedures includes a movable drive structure for propelling tissue sampling displacement of the needle assembly and a cocking structure arranged to reverse the displacement of the drive structure after the needle propulsion. A trigger structure in the actuator device cooperates with the drive structure to selectively activate the needle propulsion, and the trigger structure comprises a retention mechanism for releasably restraining the propulsion. The trigger structure also includes safety lock structure which releasably locks the activation restraint by the retention mechanism, and the cocking structure has release structure for unlocking the restraint by the retention mechanism to selectively allow operation of the trigger structure to activate propulsion by the drive structure.

In a preferred embodiment, the trigger structure has a retaining latch which restrains the drive structure in the cocked or armed position and the trigger structure also has a safety lock projection which is normally locked by the cocking structure to prevent motion of the locking projection and the trigger structure sufficient to unlatch the drive structure except in an activating position of the cocking structure. In the activating position of the cocking structure, the locking projection from the trigger structure can be unlocked to allow unlatching motion by the trigger structure to activate the propulsion by the drive structure. Manual motion of the cocking structure reversely moves the drive structure and at the same time compresses a single drive spring bearing thereon which generates the propulsion. In the activatable position of the cocking structure, a release clearance therein is located in an alignment into which the lock projection on the trigger structure can be inserted when the physician thereafter selectively deflects the trigger structure to unlatch the drive structure and propel the needle assembly in the tissue sampling operation.

BRIEF DESCRIPTION OF THE DRAWINGS

FIG. 1 is a perspective view of one embodiment of a tissue sampling instrument in accordance with the present invention;

FIG. 2 is a partially exploded, perspective view of arming and activating components in the lower portion of the instrument shown in FIG. 1;

FIG. 3 is a side view of the trigger elements of the instrument shown in FIGS. 1 and 2;

FIG. 4 is a fragmentary, partially sectional view of the trigger elements and cooperating arming components illustrated in FIGS. 1–3;

FIGS. 5–7 are sequential, partially fragmentary side views illustrating successive positions during an arming operation of the instrument shown in FIGS. 1–4.

DETAILED DESCRIPTION OF THE ILLUSTRATED EMBODIMENT

Figure 7:
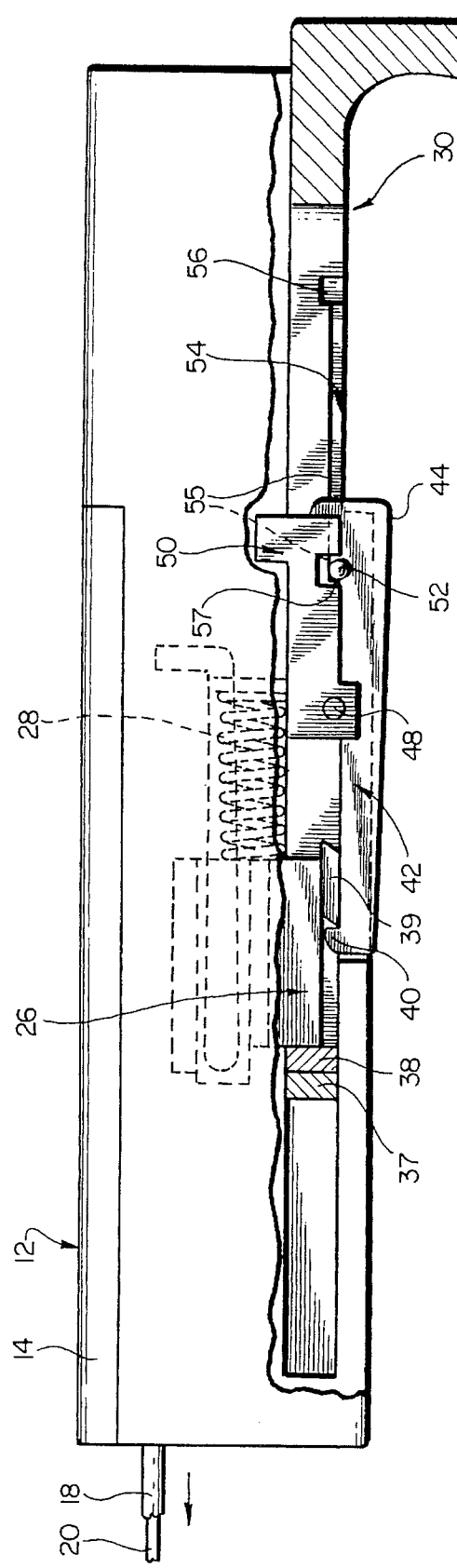

Referring to FIGS. 1 and 2, one embodiment of a tissue sampling instrument or actuator in accordance with the present invention is designated generally by reference character 10. In the illustrated embodiment 10, the actuator 10 has a housing 12 which has a hinged cover 14 that opens to enable installation and removal of a two-part needle assembly generally designated 16 conventionally includes a hollow outer cannula 18 through which a stylet 20 is slidably projected to cut and capture a core of diagnostic tissue. The cannula 18 and stylet 20 are carried on respective carriages 22 and 24 in relative movement of the tissue sampling capture. One or both of the carriages 22 and 24 are driven, in the tissue sampling operation, by a drive assembly designated generally 26 as more fully described in detail in the aforementioned U.S. Pat. No. 5,121,751. The drive assembly 26 is propelled during the tissue sampling operation by the expansion of the helical drive spring 28 from the activated position shown in FIGS. 7 and 8 to the terminal position of the drive assembly 26 shown in FIG. 5 representing completion of the tissue capturing motion of the needle assembly 16 as previously described.

Figure 8:
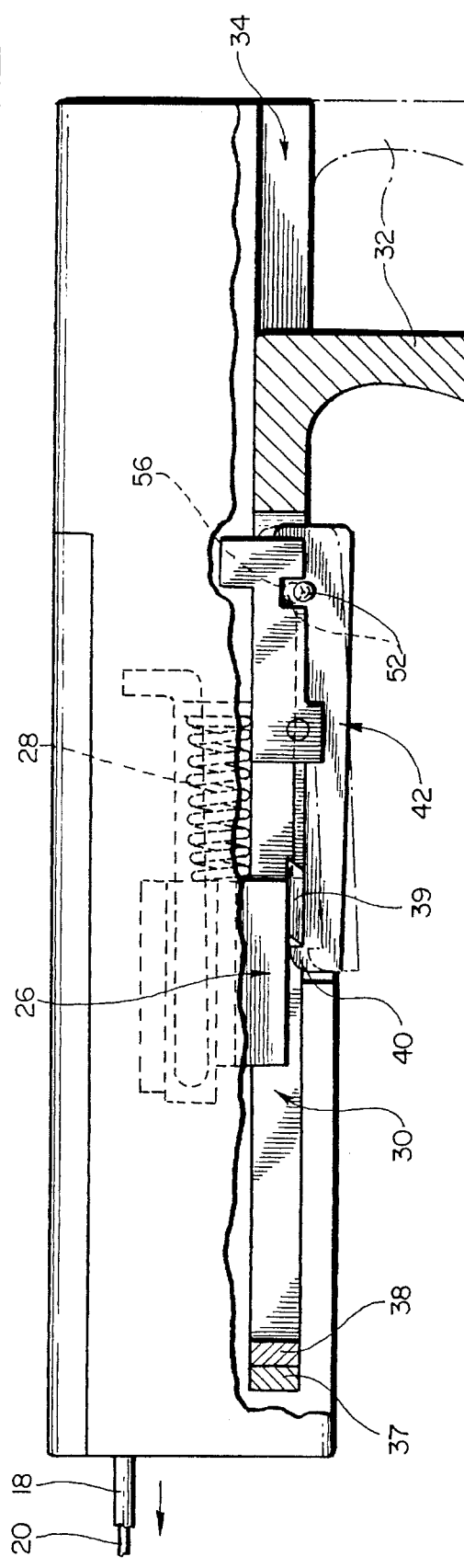
FIG. 8 is a fragmentary, partially sectional view similar to FIGS. 5–7 illustrating the activation or triggering of the armed instrument shown in FIG. 7.

The recompression of the drive spring 28 for a subsequent tissue sampling operation, is achieved by manually forcing the drive assembly 26 in a reverse motion from the terminal position in FIG. 5 to the activatable or armed position in FIGS. 7 and 8 using a manually slidable cocking member 30 which is conveniently gripped by the integral handle 32.

The cocking member 30 is forwardly and reversely slidable through a track extending above the abbreviated bottom housing wall 13, extending into an open channel 34 on the bottom rear of the housing 12. As best shown in FIG. 2, the forward end of the cocking member 30 is formed as an open rectangular frame 36 within which the drive assembly 26 is disposed, so that in the advanced, terminal position of the drive assembly 26 as shown in FIG. 5, the transverse front wall 37 carrying cushion 38 is engaged against the lower front wall of the drive assembly 26. In the cocking operation of the actuator 10 beginning as shown in FIGS. 5 and 6, manual retraction of the cocking member 30 by handle 32 through slot 34 pulls the drive assembly 26 rearwardly to force compression of the spring 28 from the position shown in FIG. 5 through the position shown in FIG. 6 until the position shown in FIG. 7 is reached at which a hook shaped end latch 40 of pivotal trigger 42 snaps upwardly behind a latch foot 39 on the bottom of the drive assembly 26, thereby latching and retaining the drive assembly 26 and the compression of the spring 28 as shown in FIG. 7. The latching hook end 40 is urged pivotally upwardly to maintain the arming latch in FIG. 7 by the downward force on the opposite end 44 of the pivotal trigger 42 imposed by the biasing tension in a helical trigger spring 46 as best shown in FIG. 3. The trigger 42 is pivotal on a pivot bearing pin 48 mounted on a support block 50 secured within the housing 12. The support block 50 also secures the anchored end of the trigger spring 46 as best shown in FIG. 3.

In order to prevent inadvertent unlatching and activated release of the drive assembly 26 by any unintentional reverse pivot of the trigger 42, a pair of lock bolts 52 laterally project from the sides of the trigger 42. As best shown in FIG. 4, a transverse internal pocket 15 in the bottom housing wall 13 provides a stop surface to limit the downward pivot of the bolts 52. The lock bolts 52 fit into a corresponding pair of longitudinal recess slots 54 formed in each of the opposing frame sides 31 of the elongate cocking member 30. The respective "roof" surfaces 55 horizontally extending above each of the slots 54 serve as safety lockstops which prevent sufficient vertically upward pivot of the lock bolts 52 to otherwise allow corresponding vertically downwardly pivot and unlatch of the trigger latch 40 during the sliding motions of the cocking member 30, until such sliding motion moves firing or activating notches 56 formed at the end on each of the slots 54, into vertical alignment to, accept manual insertion of the lock bolts 52. Thereafter, manual upward deflection on the trigger end 44, against the bias of spring 46, to upwardly pivot trigger end 44 and downwardly pivot unlatching trigger latch end 40 from drive structure foot 39. Unlatching releases motion of the drive assembly 26 from the position in FIG. 8 to the position in FIG. 5 to propel the needle assembly 16 in a tissue sampling operation. The working tolerance allows very slight upward deflection of the drive assembly 26 as the foot 39 is cammed in cocking travel over the downwardly pivoting latch end 40 as shown in FIG. 6, so that the lock bolts 52 need not pivot upwardly as far during the cocking latch of end 40, as the extent of upward pivot of the bolts 52 into the notch 56 required for the corresponding downward trigger activation pivot of the latch end 40 to unlatch from the foot 39.

Referring again to FIG. 7, when the cocking member has been retracted sufficiently to latch the drive assembly 26 in the armed position, the lock bolts 52 engage and stop the respective forward end walls 57 of the slots 54 to prevent any further retraction of the cocking member 30. Thereafter, however, in order for the physician to deflect the trigger to activate the tissue sampling propulsion by the drive structure 26, the cocking member 30 must be again slid forwardly to the position shown in FIG. 8 to advance the firing notches 56 into alignment with the respective lock bolts 52 and allow the unlocking displacement of the bolts 52 into the notches 56 with the trigger deflection. As a result, the fully retracted position of the cocking member 30 in FIG. 7 serves to arm but lock the drive structure 26 in a safety, standby condition of the actuator 10 which prevents any inadvertent unlatching thereof by unintended motion of the trigger structure 42, and only the subsequent advance of the cocking member 30 for deliberate preparation will allow trigger unlatching and activation of the needle propulsion by the drive structure 26. Optionally, either the fully retracted position of FIG. 7 or a position of the cocking structure 30 and handle 32, shown in dashed line in FIG. 8, intermediate the solid line positions of FIGS. 7 and 8, could be held by detent structure (not shown) to serve as a safety and handling convenience to prevent inadvertent sliding of the cocking member 32 into the unlocked position while preparing for actual tissue sampling operation of the actuator 10.

The advance of the cocking member 30 to the activatable position in FIG. 8 also advances and disengages the front wall 37 and cushion 38 of the cocking member 30 from the front wall of the drive structure 26 so that in the tissue sampling operation, the expansion of the drive spring 28 and motion of the drive structure 26 from the position shown in FIG. 8 to the position shown in FIG. 5 propels only the needle structure 16 without need for also carrying the cocking structure 30 which has already been advanced. The physician advances the cocking member 30 to unlock the lock bolts 52 as part of the intended safety release for activation of the tissue sampling operation.

While a preferred embodiment of the present invention is shown and described, it is envisioned that those skilled in the art may devise various modifications and equivalents without departing from the spirit and scope of the appended claims.

The invention claimed is:

1. An actuator device for propulsion of a needle assembly particularly employed for tissue sampling procedures comprising:

a movable drive structure for propelling tissue sampling displacement of a needle assembly;

a cocking structure arranged to move said drive structure between a first position in which said needle assembly displacement is terminated and a second armed position in which said needle assembly displacement can be initiated;

a trigger structure cooperable with said drive structure to selectively activate movement thereof from said second position to said first position for said needle assembly displacement;

retention means for releasably restraining activation of said drive structure movement;

lock means for releasably locking restraint of said activation by said retention means; and said cocking structure comprising release means for unlocking said restraint by said retention means to allow operation of said trigger structure to activate said drive structure movement.

2. A device according to claim 1 wherein at least a portion of said lock means is formed on said trigger structure.

3. A device according to claim 1 wherein said lock means comprises a bolt member projecting from said trigger structure.

4. A device according to claim 3 wherein said bolt member is selectively blocked by said cocking structure to prevent motion thereof sufficient to allow said trigger structure activation of said drive structure movement.

5. A device according to claim 4 wherein said cocking structure release means comprises a release clearance into which said bolt member is movable for said unlocking.

6. A device according to claim 5 wherein said cocking structure comprises a guide formation against which said bolt member is relatively slidable.

7. A device according to claim 6 wherein said release clearance is arranged adjacent said guide formation.

8. A device according to claim 7 wherein said guide formation comprises a slot formed in said cocking structure within which said bolt member is relatively slidable into a notch formed on said slot which thereon defining said clearance.

9. A device according to claim 1 wherein said trigger structure comprises support structure including pivot bearing means for supporting pivotable movement of a trigger member, the trigger member having a bolt member projecting therefrom comprised in said lock means, and said cocking means including a release clearance defining said release means, said release clearance being alignable with an opening formed in said trigger support structure said bolt member being receivable within said alignable release clearance and support member opening to achieve said unlocking and said trigger structure activation.

10. A device according to claim 1 wherein said trigger structure comprises a pivotable member having said retention means and said lock means arranged with and a pivot support formed therebetween.

11. A device according to claim 9 wherein said support structure further supports a biasing spring means for urging restraint of said activation by said retention means.

12. A device according to claim 1 wherein said trigger structure lock means comprises a lock member thereon and wherein said cocking structure is movable to carry said drive structure into said second, armed position into which said cocking structure release means allows motion of said lock member for said unlocking restraint enabling said activation by said trigger structure.

13. A device according to claim 12, wherein said lock member is blocked from said motion thereof unlocking said restraint during motion of said cocking structure until said cocking structure arrives at and carries said drive structure to said second, armed position.

* * * * *

UNITED STATES PATENT AND TRADEMARK OFFICE
CERTIFICATE OF CORRECTION

PATENT NO.  : 5,551,442
DATED       : September 3, 1996
INVENTOR(S) : Rowland W. Kanner and Richard M. Davis It is certified that error appears in the above-indentified patent and that said Letters Patent is hereby corrected as shown below:

On the title page, item [56] insert

-- 4,907,599        3/1990      Taylor ....................128/754 --

Signed and Sealed this

Eleventh Day of February, 1997

Attest:

BRUCE LEHMAN

Attesting Officer      Commissioner of Patents and Trademarks